United States Patent
Falk et al.

(10) Patent No.: US 8,580,285 B2
(45) Date of Patent: Nov. 12, 2013

(54) CLARIFYING AGENTS FOR ORGANOMODIFIED SILICONES

(75) Inventors: Benjamin Falk, Yorktown Heights, NY (US); Sigfredo Gonzalez, Danbury, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 14 days.

(21) Appl. No.: 13/156,499

(22) Filed: Jun. 9, 2011

(65) Prior Publication Data

US 2012/0315229 A1 Dec. 13, 2012

(51) Int. Cl.
*A61K 8/06* (2006.01)
*A61K 8/02* (2006.01)

(52) U.S. Cl.
USPC ............... 424/401; 424/59; 424/61; 424/63; 424/64; 424/65; 424/70.7; 424/70.12

(58) Field of Classification Search
USPC ........ 424/401, 59, 61, 63, 64, 65, 70.7, 70.12
See application file for complete search history.

(56) References Cited

U.S. PATENT DOCUMENTS

| | | | |
|---|---|---|---|
| 5,470,884 A | 11/1995 | Corless et al. | |
| 5,531,986 A | 7/1996 | Shevade et al. | |
| 6,242,396 B1 | 6/2001 | Guillou et al. | |
| 6,403,067 B1 | 6/2002 | Schamper et al. | |
| 6,426,079 B1 * | 7/2002 | Bara et al. | 424/401 |
| 6,531,540 B1 | 3/2003 | O'Brien | |
| 2002/0110532 A1 * | 8/2002 | Guskey et al. | 424/65 |
| 2005/0031560 A9 | 2/2005 | Simonnet et al. | |
| 2005/0043475 A1 | 2/2005 | Blin | |
| 2007/0128143 A1 | 6/2007 | Gruning et al. | |
| 2008/0014166 A1 * | 1/2008 | Klug et al. | 424/70.12 |
| 2010/0080766 A1 | 4/2010 | Dumousseaux et al. | |
| 2011/0104085 A1 | 5/2011 | Klug et al. | |
| 2011/0212033 A1 | 9/2011 | Tamarkin et al. | |

FOREIGN PATENT DOCUMENTS

WO 2011/064255 A1 6/2011

OTHER PUBLICATIONS

Dietz, Thomas: "A Novel Silicone-based O/W.Emulsifier with Skin Smoothing Sensation", May 1, 2002, pp. 1-7, XP002680654, Retrieved from the Internet: URL:http://personal-care.evonik.com/product/personal-care/en/media-center/downloads/publications/Documents/ct-abil-care.pdf [retrieved on Jul. 24, 2012].
Hansen, Charles M., "The Three Dimensional Solubility Parameter—Key to Paint Component Affinities: I. Solvents, Plasticizers, Polymers, and Resins", Journal of Paint Technology, vol. 39, No. 505, pp. 104-112; (Feb. 1967).

* cited by examiner

*Primary Examiner* — Margaret Moore
(74) *Attorney, Agent, or Firm* — Dominick G. Vicari; Joseph S. Ostroff

(57) ABSTRACT

There is provided herein a composition comprising a silicone copolymer of the general formula (I) $M_a M^E_c D_d D^E_e T_f T^E_g Q_h$ where $M=R^1R^2R^3SiO_{1/2}$; $M^E=R^4R^5R^ESiO_{1/2}$; $D=R^6R^7SiO_{2/2}$; $D^E=R^8R^ESiO_{2/2}$; $T=R^9R^ESiO_{2/2}$; $T=R^9SiO_{3/2}$; $T^E=R^ESiO_{2/2}$; and $Q=SiO_{4/2}$; where $R^1$, $R^2$, $R^3$, $R^4$, $R^5$, $R^6$, $R^7$, $R^8$, and $R^9$ are each independently selected from the group of monovalent hydrocarbon radicals $R^E$ is a monovalent radical defined as: $-R^{10}O-(C_2H_4O)_h(C_3H_6O)_i(C_4H_8O)_j-R^{11}$ or $-R^{12}$ with the provision that the copolymer must contain at least one $R^E$ group; $R^{10}$ is a linear or branched divalent hydrocarbon radical containing from 3 to about 10 carbon atoms; $R^{11}$ is H or $-C(=O)CH_3$ or a monovalent saturated or unsaturated hydrocarbon radical, optionally containing heteroatoms and hydroxyl groups, containing from 1 to about 30 carbon atoms; $R^{12}$ is a hydrocarbon radical, containing from 2 to about 30 carbon atoms and at least 1 hydroxyl group, optionally containing heteroatoms; subscripts a, b, c, d, e, f, and g are 0 or positive subject to the limitation a+b+c+d+e+f+g<1000; subscripts h, i, and j are 0 or positive subject to the limitation h+i+j is less than 100; and, b) an organic oil.

20 Claims, No Drawings

CLARIFYING AGENTS FOR ORGANOMODIFIED SILICONES

FIELD OF THE INVENTION

The present invention relates to compositions comprising a silicone copolymer and an organic ester, more specifically, a composition comprising a high viscosity silicone surfactant and an organic ester wherein the viscosity of the composition is below 20,000 cPs and wherein the composition exhibits a translucent appearance. The present invention also relates to a process of treating a silicone surfactant. There are also provided personal care formulations containing the composition.

BACKGROUND OF THE INVENTION

Silicone emulsifiers exhibit tremendous utility in forming water-in-oil (w/o) and oil-in-water (o/w) emulsions especially if the oil phase is predominantly silicone in nature. In the personal care field some high molecular weight silicone polyether copolymer surfactants are blended in decamethyl-cyclopentasiloxane ($D_5$) and the like. This solvent is necessary due to the extremely high viscosity of many neat silicone polyether copolymer surfactants.

Although the solvent does reduce the viscosity of the copolymer the solvent does not compatabilize the polyether segments with the silicone, resulting in a milky white appearance which is undesirable in many personal care applications. Furthermore, upon standing the silicone copolymers begin to phase separate leading to the necessity to mix the contents of the container prior to sampling. In a production environment it is difficult to mix bulk or even small storage tanks efficiently resulting in a great probability of poor emulsion stability. In order to reduce the viscosity such that the mixture is easy to handle large amount of solvents are required, which necessarily results in low concentrations of silicone copolymer surfactant. This low concentration of silicone surfactant requires the end user to use much more silicone surfactant solution in the personal care formulation to achieve a stable emulsion.

Thus, there exists a demand for an effective means of solvating high molecular weight silicone surfactants that avoids the above noted undesirable discoloration of the resulting emulsion, and does not require excessive amounts of solvent.

SUMMARY OF THE INVENTION

One objective of the present invention is directed to a composition comprising
a) a silicone copolymer of the general formula (I)

$$M_a M^E_b D_c D^E_d T_e T^E_f Q_g \qquad (I)$$

where

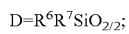

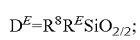

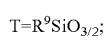

where
$R^1$, $R^2$, $R^3$, $R^4$, $R^5$, $R^6$, $R^7$, $R^8$, and $R^9$ are each independently selected from the group of monovalent hydrocarbon radicals optionally containing heteroatoms, carbonyl groups, and hydroxyl groups, each independently containing from about 1 to about 20 carbon atoms, preferably from about 1 to about 15 carbon atoms, and more preferably from about 1 to about 10 carbon atoms;

$R^E$ is a monovalent radical defined as: $-R^{10}O-(C_2H_4O)_h(C_3H_6O)_i(C_4H_8O)_j-R^{11}$ or $-R^{12}$ with the provision that the copolymer must contain at least one $R^E$ group;

$R^{10}$ is a linear or branched divalent hydrocarbon radical containing from 3 to about 10 carbon atoms;

$R^{11}$ is H, $-C(=O)CH_3$, or a monovalent saturated or unsaturated hydrocarbon radical, optionally containing heteroatoms and hydroxyl groups, containing from 1 to about 30 carbon atoms, specifically from 1 to about 10 carbon atoms, more specifically from 1 to about 3 carbon atoms;

$R^{12}$ is a hydrocarbon radical, containing from 2 to about 30 carbon atoms, specifically 8 to about 28 carbon atoms, more specifically from 12 to about 26 carbon atoms and at least 1 hydroxyl group, optionally containing heteroatoms, such as, for example O and N;

subscripts a, b, c, d, e, f, and g are zero or positive subject to the limitation a+b+c+d+e+f+g<1000, specifically, a+b+c+d+e+f+g<750 and more specifically a+b+c+d+e+f+g<600;

subscripts h, i, and j are zero or positive and are subject to the limitation h+i+j is less than 100, specifically, h+i+j is less than 80 and more specifically h+i+j is less than 60; and, b) an organic ester which exhibits Hansen solubility parameters of $14<\delta_D<18$, $4<\delta_H<10$ and $3<\delta_P<15$, more preferably $15<\delta_D<17$, $5<\delta_H<7$ and $3<\delta_P<10$, most preferably $15.5<\delta_D 21\ 17, 5 <\delta_H<7$ and $3<\delta_P<5$, and wherein the composition has a viscosity of less than 20,000 cps.

In one other objective there is provided a process of treating a silicone surfactant comprising mixing the contents of the above-noted composition wherein the mixing results in the composition having a viscosity of less than 20,000 cps.

The present invention is further described in the detailed description section provided below.

DETAILED DESCRIPTION OF THE INVENTION

It has been unexpectedly discovered by the inventors herein that organic esters which exhibit Hansen solubility parameters of $14<\delta_D<18$, $4<\delta_H<10$ and $3<\delta_P<15$ can effectively solvate high molecular weight silicone copolymer surfactants and lower the viscosity of the resultant emulsion to less than 20,000, which provides for easy handling. In addition, these organic ester(s) described herein, provide for greatly improved shelf stability, as well as translucency of the resultant emulsion, and specifically can provide this in the absence of water in the emulsion.

In the specification and claims herein, the following terms and expressions are to be understood as indicated.

As used in the specification and including the appended claims, the singular forms "a," "an," and "the" include the plural, and reference to a particular numerical value includes at least that particular value, unless the context clearly dictates otherwise.

Ranges expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

Other than in the working examples or where otherwise indicated, all numbers expressing amounts of materials, reaction conditions, time durations, quantified properties of materials, and so forth, stated in the specification and claims are to be understood as being modified in all instances by the term "about."

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The expression "hydrocarbon radicals" means any hydrocarbon group from which one or more hydrogen atoms has been removed and is inclusive of alkyl, alkenyl, alkynyl, cyclic alkyl, cyclic alkenyl, cyclic alkynyl, aryl, aralkyl and arenyl and may contain heteroatoms.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

The expression "organic ester" is understood to mean an organic compound comprising at least one ester functional group.

It will be understood herein that all measures of viscosity are obtained at 25 degrees Celsius unless noted otherwise.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

In one non-limiting embodiment herein the silicone copolymer (a) may be a silicone surfactant such as those which are commercially available and/or used in personal care formulations.

In one specific embodiment $R^1$-$R^9$ may each independently be a hydrocarbon radical of from 1 to 4 carbon atoms such as methyl, ethyl, propyl, isopropyl, butyl and isobutyl.

In another specific embodiment, the subscripts a, b, c and d may each be greater than zero. The silicone copolymer (a) may also be such that subscript a may be two and subscript b may be zero and subscript c may be from 100 to 750, specifically from 250 to 600 and more specifically from 440 to 550, subscript d is from 1 to 10, specifically from 2 to 8 and most specifically from 4 to 7, subscripts b, e, f and g are each zero.

In yet another specific embodiment, the silicone copolymer (a) may be such that subscript a may be zero and subscript b may be 2 and subscript c may be from 100 to 750, specifically from 250 to 600 and more specifically from 440 to 550, subscript d is from 1 to 10, specifically from 2 to 8 and most specifically from 4 to 7, subscripts e, f and g are each zero.

In one other embodiment, the silicone copolymer (a) may be such that subscript a may be one and subscript b may be one and subscript c may be from 100 to 750, specifically from 250 to 600 and more specifically from 440 to 550, subscript d is from 1 to 10, specifically from 2 to 8 and most specifically from 4 to 7, subscripts e, f and g are each zero.

In one more embodiment, the silicone copolymer (a) may be such that subscript a may be two, subscript b may zero, subscript c may be from 1 to 150, specifically from 50 to 135, more specifically from 80 to 130, subscript d is from 1 to 30, specifically from 10 to 28 and most specifically from 20 to 26, subscripts e, f and g are each zero.

$R^E$ may in one specific embodiment be defined by the formula: $-R^{10}O-(C_2H_4O)_h(C_3H_6O)_i(C_4H_8O)_j-R^{11}$ where $R^{10}$, $R^{11}$, h, i and j are as defined. Specifically, $R^{10}$ may be a linear divalent hydrocarbon radical of from 3 to about 6 carbon atoms, more specifically, propyl and subscript h may be from 10 to about 30, more specifically from 15 to about 25, and subscript i may be from 8 to 20, more specifically from 12 to 18, and subscript j may be zero and $R^{11}$ may be H.

In one specific embodiment silicone copolymer (a) may be of the formula:

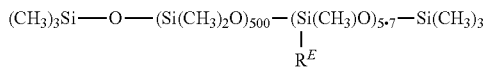

wherein $R^E$ may be of the formula:

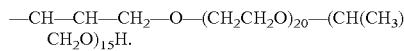

$R^E$ may in one other specific embodiment be defined by the formula —$R^{12}$ which may be a monovalent hydrocarbon radical of from 2 to 15 carbon atoms and containing from 1 to about 8 hydroxyl groups, specifically from 1 to about 6 hydroxyl groups and one oxygen heteroatom and one nitrogen heteroatom.

—$R^{12}$ may in one example have the formula:

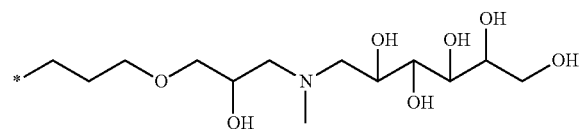 [SMILES: *CCCOCC(O)CN(C)CC(O)C(O)C(O)C(O)CO]

$R^{12}$ may in another embodiment be a monovalent hydrocarbon radical of from 2 to 25 carbon atoms and containing 1 hydroxyl group, a carbonyl and two oxygen heteroatoms.

—$R^{12}$ may in one example have the formula:

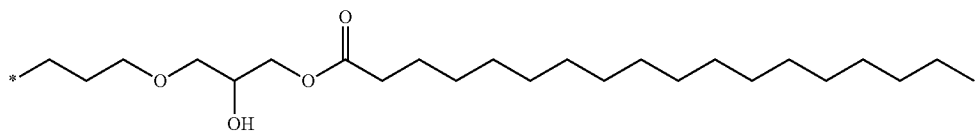 [SMILES: *CCCOCC(O)COC(=O)CCCCCCCCCCCCCCCCC]

In one embodiment silicone copolymer (a) can have the formula:

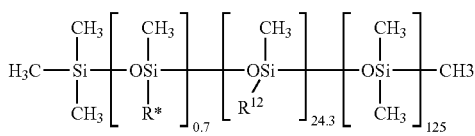

wherein R* is

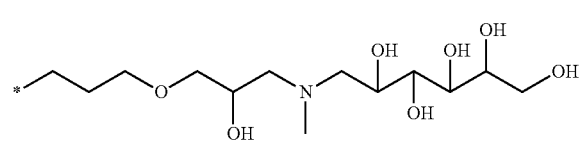 [SMILES: *CCCOCC(O)CN(C)CC(O)C(O)C(O)C(O)CO]

and $R^{12}$ is

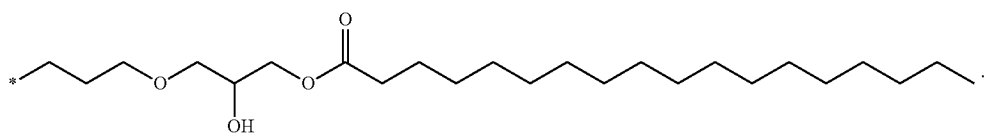 [SMILES: *CCCOCC(O)COC(=O)CCCCCCCCCCCCCCCCC]

In one non-limiting embodiment herein the silicone copolymer (a) can have a viscosity of greater than 20,000 cps, specifically greater than 50,000 cps and most specifically greater than 100,000 cps, each of these ranges in one embodiment having an upper endpoint of 2,000,000 cps.

It will be understood herein that the organic ester (b) chosen according to the noted solubility parameters herein is due to the inventors have unexpectedly discovered herein that organic ester(s) that fall within these solubility parameters provide for significantly decreased viscosity in the resultant emulsion over identical compositions which contain organic esters other than those of the present invention, prolonged shelf-stability over identical compositions which contain organic esters other than those of the present invention and decreased color over identical compositions which contain organic esters other than those of the present invention.

In one non-limiting example the organic ester (b) used herein may be other than any of comparative organic esters described in the examples section herein.

Some non-limiting examples of organic ester (b) that may be employed herein are those selected from the group consisting of myristal proprionate, neopentylglycol dioctanoate, diethylhexyl maleate, diisopropyl adipate, caprylic/capric triglyceride, diacetyl maleate, dicaprylyl maleate, diisopropryl sebacate, diethyl malonate, diethyl oxalate, dimethyl adipate, dimethyl maleate, dibutyl sebacate, dibutyl fumarate, dipropyl oxalate, decanedioic acid diethyl ester, dibenzyl malonate, dipropyl glutarate, diethyl Succinate; and, combinations thereof.

The Hansen solubility parameters $\delta_D$, $\delta_H$ and $\delta_P$ of the organic ester(s) (b) used herein, and the means of calculating the same at 25 degrees Celsius are described both in the article by C. M. Hansen: "*The three dimensional solubility parameters*" J. Paint Technol. 39, 105 (1967), and *Hansen Solubility Parameters, A User's Handbook* by Charles M. Hansen, CRC Press Boca Raton Fla. (2007), both of which are specifically incorporated by reference herein.

$\delta_D$ characterizes the dispersive cohesive forces (such as nonpolar interactions);

$\delta_H$ characterizes the specific interaction forces (such as hydrogen bonding, acid/base, donor/acceptor, etc. interactions);

$\delta_P$ characterizes the Debye interaction forces between permanent dipoles and the Keesom interaction forces between induced dipoles and permanent dipoles. The solubility parameters $\delta_D$, $\delta_H$ and $\delta_P$ are expressed in units of $Mpa^{1/2}$.

The resulting mixture will exhibit a viscosity less then 20,000 cps, preferably less then 15,000 cps, more preferably less than 10,000 cps. In one embodiment, the composition herein has a viscosity of from about 1,000 to about 5,000 cps.

The compositions herein can be formulated as clear, translucent or opaque compositions and also the personal care products (formulations) that employ the composition herein or the silicone emulsion containing the composition noted herein. Clear compositions and products are preferred. A desired feature of the present invention is that a clear or transparent personal care composition (e.g., a cosmetic composition) can be provided. The term clear or transparent according to the present invention is intended to connote its usual dictionary definition; thus, a clear personal care composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass there through. Thus, according to the present invention, there are differences between transparent (clear), translucent and opaque compositions. These differences can be noted by the naked eye in the manner indicated herein and as is known to those skilled in the art.

In another embodiment herein the composition, the silicone emulsion containing the composition and any personal care formulation containing the composition or silicone emulsion can have an improved shelf stability over identical compositions which do not employ the organic ester (b) described herein. In one non-limiting embodiment the composition, the silicone emulsion containing the composition and any personal care formulation containing the composition or silicone emulsion can have a shelf stability of at least one month, specifically at least 3 months and more specifically at least six months.

The stability of the emulsions may be measured by visually evaluating the emulsion for phase separation and/or by other methods that are known in the art for evaluating phase separation which will not be discussed herein. While it has been found that the organic ester (b) emulsifies the silicone copolymer (a) into a stable emulsion that has the shelf-stability noted herein, such emulsions are not so stable that they do not provide for the desired personal care application for which they are being used.

In one non-limiting embodiment herein, the composition, the silicone emulsion containing the composition and any personal care formulation containing the composition or silicone emulsion can be in the absence of water. In yet another embodiment, the composition, the silicone emulsion containing the composition and any personal care formulation containing the composition or silicone emulsion can be in the absence of any and all minor amounts of water that is used in compositions outside the scope of the invention herein.

In one embodiment herein the amount of silicone copolymer (a) can be at least about 10 weight percent, specifically at least about 30 weight percent and most specifically at least about 60 weight percent, based on the total weight of the composition. In another embodiment the amount of organic ester (b) can be up to about 90 weight percent, specifically up to about 60 weight percent and most specifically up to 40 weight percent, based on the total weight of the composition. It will be understood that the amount of silicone copolymer (a) and organic ester (b) cannot exceed 100 weight percent of the composition.

In one further embodiment herein there is provided an emulsion which contains the composition described herein. Specifically, this emulsion is a non-aqueous silicone emulsion, more specifically a non-aqueous silicone emulsion which is typically used in personal care formulations. There is also provided a personal care composition comprising the non-aqueous silicone emulsion which contains the composition herein. In another embodiment, the personal care composition can comprise the composition herein.

In one embodiment, there is provided a personal care formulation comprising the composition as described herein where said personal care formulation is at least one non-limiting example such as those selected from the group consisting of deodorant, antiperspirant, antiperspirant/deodorant, shaving product, skin lotion, moisturizer, toner, bath product, cleansing product, hair care product such as shampoos, conditioners, mousses, styling gels, hair sprays, hair dyes, hair color products, hair bleaches, waving products, hair straighteners, hair frizz control; hair volumizing; manicure product such as nail polish, nail polish remover, nails creams and lotions, cuticle softeners, protective cream such as sunscreen, insect repellent and anti-aging products, color cosmetic such as lipsticks, foundations, face powders, eye liners, eye shadows, blushes, makeup, mascaras, as vehicles for fragrance delivery benefits, and other personal care formulations where silicone components have been conventionally added, as well as drug delivery system for topical application of medicinal composition that is to be applied to the skin.

In a more specific embodiment, the personal care composition (formulation or product) described herein further comprises one or more personal care ingredients. Suitable personal care ingredients include, for example, emollient, moisturizer, humectant, pigment, including pearlescent pigments such as, for example, bismuth oxychloride and titanium dioxide coated mica, colorant, fragrance, biocide, preservative, antioxidant, anti-microbial agent, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, thickening agent such as, for example, fumed silica or hydrated silica, particulate filler, such as for example, talc, kaolin, starch, modified starch, mica, nylon, clay, such as, for example, bentonite and organo-modified clays, and combinations thereof.

There is also provided herein a process of treating a silicone surfactant which can comprise mixing the contents of the composition described herein.

The incorporation of the organic ester (b) into the silicone copolymer (a) can be achieved by any method known in the art for integrally mixing solvents with surfactants. The mixing procedure can use, for example, standard mixers, high-speed mixers or blenders, or shakers. The temperature can be unadjusted within room temperature limits (~20-40° C.), or adjusted as required, for example, to 40-150° C. for a suitable amount of time.

The emulsification of silicone copolymer (a) by organic ester (b) can be conducted in any of the herein described mixing procedures or those which are known in the art, and specifically wherein the noted mixers, blenders or shakers are located in a continuous or batch production line and/or within a larger industrial apparatus.

Further details of methods of emulsification are well known in the art and shall not be detailed herein.

In one embodiment the composition is clear or translucent following mixing of the contents of the composition. The mixed composition, emulsion containing the composition or personal care formulation containing the emulsion or the composition directly can have the noted shelf stability and can be in the absence of water as discussed herein.

EXAMPLES

Synthesis Example 1

Synthesis of Silicone Polyether Copolymer

An allylfunctional polyether with the average structure of $CH_2=CHCH_2O(CH_2CH_2O)_{20}(CH(CH_3)CH_2O)_{15}H$ (80.7 g), a silicone hydride fluid with the average structure $(CH_3)_3SiO(Si(CH_3)_2O)_{500}(Si(CH_3)(H)O)_{5.7}Si(CH_3)_3$ (169.3 g), isopropanol (107.14 g) and sodium propionate (0.025 g) were added to the round bottom flask. The mixture was heated to 85° C. Chloroplatinic acid solution in ethanol (CPA catalyst, 10 ppm Pt) was added and the flask was stirred under nitrogen. Only a slight exotherm was noticed. The product was held at 85° C. for 1.5 hrs. No Si—H was detectable in the infrared chromatogram. The fluid was clear with a brown tint due to the Pt. The resulting clear brown solvated copolymer was 67.0% solids with a viscosity of 1650 cP.

Application Example of Synthesis Example 1

Solvent Exchange

The hydrosilylated copolymer (67.16% Actives) in IPA (96.96 g) and solvent (43.41 g) was added to the round bottom flask. A nitrogen purge was turned on. The product was heated to 75° C. A nitrogen sparge was turned on with vigorous bubbling. Began pulling a vacuum after 42 minutes and started stripping IPA. After 7 additional minutes the pressure of the reactor was 54 Torr. The product was held with a nitrogen sparge, overhead stirring at 120° C. and 51 Torr for an additional 2 hours. The resulting physical properties of the blend are found in Table 1 below. Comparative Examples are shown in Table 2.

TABLE 1

Examples

| Solvent | Hansen Solubility Parameter | | | Viscosity | Appearance |
|---|---|---|---|---|---|
| | D | P | H | cP | |
| Myristal Propionate | 16.3 | 2.3 | 3.8 | 1146 | Hazy Lt-Med Plat. |
| Neopentylglycol Dioctanoate | 16.1 | 4.2 | 4.9 | 2470 | Hazy Lt-Med Plat. |
| Diethylhexyl Maleate | 16.2 | 3.8 | 6.2 | 5270 | Clear Lt Plat. |
| Diisopropyl Adipate | 16 | 4.2 | 6 | 3640 | Clear Lt Plat. |
| Caprylic/Capric Tryglyceride | 16.4 | 4.1 | 4 | 8900 | SI Haze Lt-Med Plat. |
| Diacetyl Maleate | 16.5 | 14.1 | 10.7 | 5240 | SI Haze Lt-Med Plat. |
| Dicaprylyl Maleate | 16.4 | 3.4 | 5.1 | 4770 | SI Haze Lt-Med Plat. |
| Diisopropyl sebacate | 16.2 | 3.2 | 5 | 3700 | SI Haze Lt-Med Plat. |

TABLE 2

Comparative Examples

| Solvent | Hansen Solubility Parameter | | | Viscosity | Appearance |
|---|---|---|---|---|---|
| | D | P | H | cP | |
| Polyglyceryl-4-Isostearate | 16.4 | 16.4 | 24.2 | 43800 | Cloudy Lt Gray |
| Decyl Oleate | 16.3 | 2.2 | 3 | 60000 | Cloudy Lt Plat. |
| Isononylisononanoate | 16.2 | 2.2 | 3.7 | 1776 | Cloudy Lt Plat. |

TABLE 2-continued

Comparative Examples

| Solvent | Hansen Solubility Parameter | | | Viscosity | Appearance |
|---|---|---|---|---|---|
| | D | P | H | cP | |
| Isononylisononanoate | 16.2 | 2.2 | 3.7 | 1776 | Cloudy Lt Plat. |
| Isopropyl Myristate | 16.2 | 2.3 | 3.8 | 1224 | Cloudy Lt Plat. |
| Di-N-Octyl Carbonate | 16.1 | 4.5 | 2.6 | 1410 | Cloudy Lt-Med Plat. |
| Isopropyl Palmitate | 16.2 | 3.9 | 3.9 | 1430 | Cloudy Med Plat. |
| Isoeicosane | 16.1 | 0.8 | 1.7 | 115200 | Hazy Lt Gray |
| Isostearyl Palmitate | 16.5 | 1.3 | 3 | NA | Lumpy |
| Decamethylcyclosiloxane | 12.9 | 1.3 | 0.5 | 204800 | White |
| Cetearyl Octanoate | 16.4 | 1.7 | 3.1 | 2460 | Cloudy Gray |
| Diethylhexylcyclohexane | 15.9 | 1.3 | 2.1 | 180200 | Cloudy Gray |

Synthesis Example 2

Synthesis of Silicone Copolymer Free of Polyether

Stearic acid (85.07 g, 300 mmol), 1.25 g triethyl amine and 164.9 g (300 mmol epoxy groups) of a siloxane of the structure

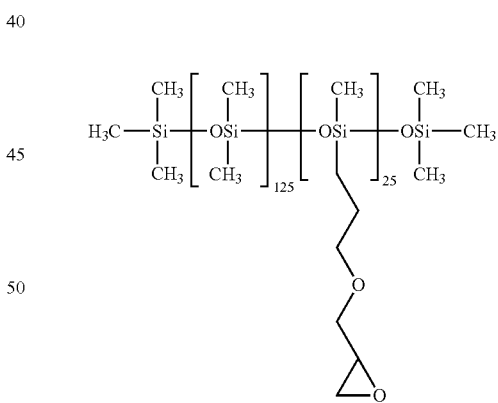

were dissolved in 107 g of propylene glycol monomethylether and heated for 10 hours to 120 ° C. The conversion was 97.1% of the epoxy groups determined via $^1$H-NMR. Subsequently, 5.84 g (30 mmol) N-methylglucamine was added and the reaction medium was held for 4 hours at 120° C. Epoxy group conversion was 100%. After completion of the reaction the volatile components were removed in vacuum at 70° C./20 mbar within 2 hours.

A yellow grey waxy polymer of the average structure

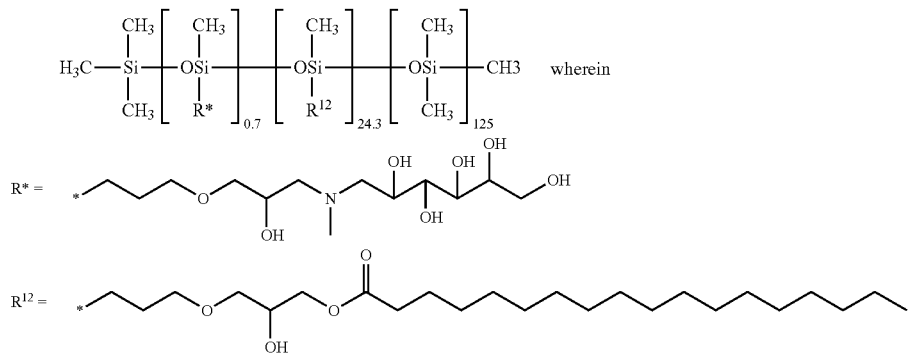

Application Example of Synthesis Example 2

Mixing Procedure

The product of synthetic example 2 (18g) was mixed with 12 g of solvent using a speedmixed model DACISOFV2 from Flack-Tec (Landrum SC) for 2 minutes at 2000 rpm. Results are reported in Table 3.

TABLE 3

| Solvent | Hansen Solubility Parameter | | | Viscosity | |
|---|---|---|---|---|---|
| | D | P | H | cP | Appearance |
| Diethylhexyl Maleate | 16.2 | 3.8 | 6.2 | 920 | SI Haze Lt-Med Plat. |
| Diisopropyl Adipate | 16 | 4.2 | 6 | 280 | SI Haze Lt-Med Plat. |

If the product was opaque or the viscosity was greater than 20,000 cps the mixture was considered to have failed.

While the invention has been described with reference to a preferable embodiment, those skilled in the art will understand that various changes may be made and equivalents may be substituted for elements thereof without departing from the scope of the invention. It is intended that the invention not be limited to the particular embodiment disclosed as the best mode for carrying out this invention, but that the invention will include all embodiments falling within the scope of the appended claims. All citations referred herein are expressly incorporated herein by reference.

What is claimed is:

1. A composition comprising
   a) a silicone copolymer of the general formula (I)

$$M_a M^E_b D_c D^E_d T_e T^E_f Q_g \quad (I)$$

where $M = R^1 R^2 R^3 SiO_{1/2}$;

$M^E = R^4 R^5 R^E SiO_{1/2}$;

$D = R^6 R^7 SiO_{2/2}$;

$D^E = R^8 R^E SiO_{2/2}$;

$T = R^9 SiO_{3/2}$;

$T^E = R^E SiO_{2/2}$; and $Q = SiO_{4/2}$;

where
   $R^1$, $R^2$, $R^3$, $R^4$, $R^5$, $R^6$, $R^7$, $R^8$, and $R^9$ are each independently selected from the group of monovalent hydrocarbon radicals optionally containing heteroatoms, carbonyl groups, and hydroxyl groups, each independently containing from about 1 to about 20 carbon atoms;
   $R^E$ is a monovalent radical defined as: $-R^{10}O-(C_2H_4O)_h(C_3H_6O)_i(C_4H_8O)_j-R^{11}$ or $-R^{12}$ with the provision that the copolymer must contain at least one $R^E$ group;
   $R^{10}$ is a linear or branched divalent hydrocarbon radical containing from 3 to about 10 carbon atoms;
   $R^{11}$ is H, $-C(=O)CH_3$, or a monovalent saturated or unsaturated hydrocarbon radical, optionally containing heteroatoms and hydroxyl groups, containing from 1 to about 30 carbon atoms;
   $R^{12}$ is a hydrocarbon radical, containing from 2 to about 30 carbon atoms and at least 1 hydroxyl group, optionally containing heteroatoms;
   subscripts a, b, c, d, e, f, and g are zero or positive subject to the limitation a+b+c+d+e+f+g<1000;
   subscripts h, i, and j are zero or positive and are subject to the limitation h+i+j is less than 100; and,
   b) an organic ester selected from the group consisting of myristal proprionate, neopentylglycol dioctanoate, diethylhexyl maleate, diisopropyl adipate, diacetyl maleate, dicaprylyl maleate, diisopropryl sebacate, diethyl malonate, diethyl oxalate, dimethyl adipate, dimethyl maleate, dibutyl sebacate, dibutyl fumarate, dipropyl oxalate, decanedioic acid diethyl ester, dibenzyl malonate, dipropyl glutarate, diethyl succinate and combinations thereof, and which exhibits Hansen solubility parameters of $14<\delta_D<18$, $4<\delta_H<10$ and $3<\delta_P<15$, and wherein the composition has a viscosity of less than 20,000 cps at room temperature,
   wherein the amount of silicone copolymer (a) is at least about 40 weight percent based on the total weight of the composition.

2. The composition of claim 1 wherein the composition has a viscosity of less than 15,000 cps.

3. The composition of claim 1 wherein the composition has a viscosity of less than 10,000 cps.

4. The composition of claim 1 wherein the composition has a viscosity of from about 1,000 to about 5,000 cps.

5. The composition of claim 1 wherein the composition is translucent.

6. The composition of claim 1 wherein the composition is clear.

7. The composition of claim 1 wherein the composition has a shelf stability of at least one month.

8. The composition of claim 1 wherein the composition is in the absence of water.

9. The composition of claim 1 wherein the composition is translucent, has a shelf stability of at least one month, and is in the absence of water.

10. The composition of claim 1 wherein the silicone copolymer (a) has a viscosity of greater than 20,000 cps at room temperature.

11. A non-aqueous silicone emulsion comprising the composition of claim 1.

12. A personal care composition comprising the non-aqueous silicone emulsion of claim 11.

13. The personal care composition of claim 12 selected from the group consisting of deodorant, antiperspirant, antiperspirant/deodorant, shaving product, skin lotion, moisturizer, toner, bath product, cleansing product, hair product, shampoo, conditioner, mousse, styling gel, hair spray, hair dye, hair color product, hair bleach, waving product, hair straightener, hair frizz control product; hair volumizing product; manicure product, nail polish, nail polish remover, nail cream and lotion, cuticle softener, sunscreen, insect repellent and anti-aging product, color cosmetic, lipstick, foundation, face powder, eye liner, eye shadow, blush, makeup, mascara, and other personal care formulations where silicone components have been conventionally added, and drug delivery system for topical application of medicinal composition that is to be applied to the skin.

14. A process of treating a silicone surfactant comprising mixing the contents of a composition, wherein the composition comprises (a) a silicone copolymer of the general formula (I):

$$M_a M^E_b D_c D^E_d T_e T^E_f Q_g \qquad (I)$$

where $M = R^1 R^2 R^3 SiO_{1/2}$;

$M^E = R^4 R^5 R^E SiO_{1/2}$;

$D = R^6 R^7 SiO_{2/2}$;

$D^E = R^6 R^E SiO_{2/2}$;

$T = R^9 SiO_{3/2}$;

$T^E = R^E SiO_{2/2}$; and $Q = SiO_{4/2}$;

where $R^1$, $R^2$, $R^3$, $R^4$, $R^5$, $R^6$, $R^7$, $R^8$, and $R^9$ are each independently selected from the group of monovalent hydrocarbon radicals optionally containing heteroatoms, carbonyl groups, and hydroxyl groups, each independently having from about 1 to about 20 carbon atoms, preferably from about 1 to about 15 carbon atoms and more preferably from about 1 to about 10 carbon atoms;

$R^E$ is a monovalent radical defined as: $-R^{10}O-(C_2H_4O)_h(C_3H_6O)_i(C_4H_8O)_j-R^{11}$ or $-R^{12}$ with the provision that the copolymer must contain at least one $R^E$ group;

$R^{10}$ is a linear or branched divalent hydrocarbon radical containing from 3 to about 10 carbon atoms;

$R^{11}$ is H, $-C(=O)CH_3$, or a monovalent saturated or unsaturated hydrocarbon radical, optionally containing heteroatoms and hydroxyl groups, having from 1 to about 30 carbon atoms;

$R^{12}$ is a hydrocarbon radical, containing from 2 to about 30 carbon atoms and at least 1 hydroxyl group, optionally containing heteroatoms;

subscripts a, b, c, d, e, f, and g are zero or positive subject to the limitation a+b+c+d+e+f+g<1000;

subscripts h, i, and j are zero or positive and are subject to the limitation h+i+j is less than 100; and, b) an organic ester selected from the group consisting of myristal proprionate, neopentylglycol dioctanoate, diethythexyl maleate, diisopropyl adipate, diacetyl maleate, dicaprylyl maleate, diisopropryl sebacate, diethyl malonate, diethyl oxalate, dimethyl adipate, dimethyl maleate, dibutyl sebacate, dibutyl fumarate, dipropyl oxalate, decanedioic acid diethyl ester, dibenzyl malonate, dipropyl glutarate, diethyl succinate and combinations thereof, and which exhibits Hansen solubility parameters of $14<\delta_D<18$, $4<\delta_H<10$ and $3<\delta_P<15$, wherein the mixing results in the composition having a viscosity of less than 20,000 cps at room temperature and, wherein the amount of silicone copolymer (a) is at least about 40 weight percent based on the total weight of the composition.

15. The process of claim 14 wherein the composition is translucent following mixing.

16. The process of claim 14 wherein the composition has a shelf stability of at least one month following mixing.

17. The process of claim 14 wherein the composition is in the absence of water.

18. The process of claim 14 wherein the composition is translucent and has a shelf stability of at least one month following mixing.

19. The composition comprising a silicone copolymer (a) having the formula:

$$(CH_3)_3Si-O-(Si(CH_3)_2O)_{500}-(Si(CH_3)O)_{5.7}-Si(CH_3)_3$$
$$\underset{R^E}{|}$$

wherein $R^E$ may be of the formula:

$$-CH-CH-CH_2-O-(CH_2CH_2O)_{20}-(CH(CH_3)CH_2O)_{15}H$$

and, b) an organic ester which exhibits Hansen solubility parameters of $14<\delta_D<18$, $4<\delta_H<10$ and $3<\delta_P<15$ and wherein the composition has a viscosity of less than 20,000 cps at room temperature.

20. A composition comprising a silicone copolymer (a) having the formula:

$$H_3C-\underset{CH_3}{\overset{CH_3}{\underset{|}{Si}}}-\left[O\underset{R^*}{\overset{CH_3}{\underset{|}{Si}}}\right]_{0.7}-\left[O\underset{R^{12}}{\overset{CH_3}{\underset{|}{Si}}}\right]_{24.3}-\left[O\underset{CH_3}{\overset{CH_3}{\underset{|}{Si}}}\right]_{125}-CH3$$

wherein R* is of the formula:

$$R^* = *\!\!\sim\!\!\sim\!\!O\!-\!CH_2\!-\!\underset{OH}{\overset{}{CH}}\!-\!CH_2\!-\!N\!\left(\!\!\begin{array}{c}CH_2\!-\!\underset{OH}{\overset{OH}{CH}}\!-\!\underset{OH}{\overset{}{CH}}\!-\!\underset{OH}{\overset{OH}{CH}}\!-\!CH_2\!-\!OH\end{array}\!\!\right)$$

and $R^{12}$ is of the formula:
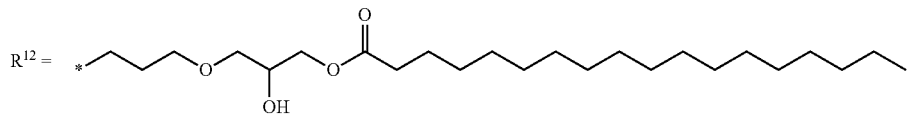 [SMILES: *CCCOCC(O)COC(=O)CCCCCCCCCCCCCCCCC]
and,
b) an organic ester which exhibits Hansen solubility parameters of $14<\delta_D<18$, $4<\delta_H<10$ and $3<\delta_P<15$, and wherein the composition has a viscosity of less than 20,000 cps at room temperature.
* * * * *